(12) United States Patent
Astatke et al.

(10) Patent No.: US 7,265,213 B2
(45) Date of Patent: Sep. 4, 2007

(54) METHODOLOGY OF CONJUGATING CHELATORS TO BIOMOLECULES

(75) Inventors: Mekbib Astatke, Gaithersburg, MD (US); Gordana Pajkovic, Alphareta, GA (US); Danielle Lynee Russell, Gaithersburg, MD (US)

(73) Assignee: KPL, Inc., Gaithersburg, MD (US)

( * ) Notice: Subject to any disclaimer, the term of this patent is extended or adjusted under 35 U.S.C. 154(b) by 0 days.

(21) Appl. No.: 11/191,001

(22) Filed: Jul. 28, 2005

(65) Prior Publication Data

US 2007/0026535 A1    Feb. 1, 2007

(51) Int. Cl.
- *C07K 1/10* (2006.01)
- *C01B 21/16* (2006.01)
- *C07D 213/00* (2006.01)
- *G01N 33/532* (2006.01)
- *G01N 33/20* (2006.01)

(52) U.S. Cl. ............ 530/409; 530/410; 436/544; 436/73; 423/407; 546/297

(58) Field of Classification Search ........... 530/409, 530/402, 391.5; 436/546, 523, 735, 544, 436/73; 435/7.5; 423/407; 546/297
See application file for complete search history.

(56) References Cited

U.S. PATENT DOCUMENTS

| | | | |
|---|---|---|---|
| 4,569,794 A | 2/1986 | Smith et al. | |
| 4,741,900 A | 5/1988 | Alvarez et al. | |
| 5,047,513 A | 9/1991 | Dobeli et al. | |
| 5,284,933 A | 2/1994 | Dobeli et al. | |
| 5,310,663 A | 5/1994 | Dobeli et al. | |
| 5,674,677 A | 10/1997 | Peterson | |
| 5,696,239 A * | 12/1997 | Wilson et al. | 534/10 |
| 5,756,685 A | 5/1998 | Fritzberg et al. | |
| 6,479,300 B1 | 11/2002 | Jiang et al. | |
| 2003/0013857 A1* | 1/2003 | Schwartz | 530/408 |
| 2004/0110730 A1* | 6/2004 | Schwartz | 514/151 |
| 2004/0156780 A1 | 8/2004 | Dadachova et al. | |
| 2005/0010038 A1* | 1/2005 | Liu | 534/11 |

OTHER PUBLICATIONS

Schutte et al., Development of acid-sensitive platinum (II) complexes with protein-binding properties. Metal-Based Drugs 2000, vol. 7, Issue 2, pp. 89-100.*

Blankespoor et al. Dense monolayers of metal-chelating ligands covalently attached to carbon electrodes electrochemically and their useful application in affinity binding of histidine-tagged proteins. Langmuir 2005, vol. 21, pp. 3362-3375.*

Blankespoor et al., "Dense Monolayers of Metal-Chelating Ligands Covalently . . . Histidine-Tagged Proteins", Americal Chem. Soc., 2005, pp. 3362-3375, vol. 21.

Schutte et al., "Development of Acid-Sensitive Plantinum(II) Complexes with Protein-Binding Properties", Dev. of Acid-Sensitive . . . Properties, 2000, pp. 89-100, vol. 7 (2).

Clontech Laboratories, Inc., "Glutathione Resins User Manual", Protocol No. PT3306-1, 2001, pp. 1-15, Version PR15765.

* cited by examiner

*Primary Examiner*—Long V. Le
*Assistant Examiner*—Shafiqul Haq
(74) *Attorney, Agent, or Firm*—Proskauer Rose LLP

(57) ABSTRACT

A novel method of conjugating chelators to biomolecules such as proteins is provided. More particularly, the invention provides compositions and methods of using those compositions for the detection, purification and transport of divalent metal cation binding biomolecules.

4 Claims, 6 Drawing Sheets

METHODOLOGY OF CONJUGATING CHELATORS TO BIOMOLECULES

FIELD OF THE INVENTION

This invention provides novel compositions and methods for conjugating metal chelating moieties to biomolecules such as proteins. More particularly, the invention provides compounds comprising a chelator and crosslinker and methodology for conjugating those compounds to biomolecules. The resulting conjugates facilitate the detection, purification and transport of biomolecules that contain divalent metal cation binding moieties.

BACKGROUND OF THE INVENTION

Overexpression of recombinant proteins in host systems is a very common tool in modern biotechnology. Following expression the recombinant proteins are detected, isolated and purified. Recently, purification and detection of the proteins has been simplified by the use of fusion tags. Commonly used fusion tags include the polyhistidine tag and GST tag (Smith et al., (1988) Gene 67:31-40; U.S. Pat. Nos. 5,284,933; and 5,310,663). An advantage of polyhistidine tags is that they can readily be coordinated with divalent metal cations such as nickel, cobalt, copper and zinc and the divalent cations can then be coordinated with a chelating agent which in turn can be coupled to a suitable probe or matrix. (US 2005/0123932 A1; U.S. Pat. No. 5,674,677; U.S. Pat. No. 4,569,794, U.S. Pat. No. 5,047,513 and U.S. Pat. No. 6,479,300).

A variety of biological applications such as in vitro and in vivo diagnostic assays and in vivo therapies require methods of detecting, purifying and transporting biomolecules such as proteins, peptides, oligonucleotides, carbohydrates, etc. A number of techniques have been developed in the past to address these issues (Greg T. Hermanson, *Bioconjugate Techniques,* Academic Press). Traditional detection techniques utilize radioactive isotopes or fluorescent compounds to monitor probe-target interactions.

Enzyme linked immunosorbent assays (ELISAs) are widely used methods for diagnosing a wide variety of disease states in man and animals, especially those diseases which are characterized by the presence of specific antibodies in the serum. Immunoblot assays are also commonly used to detect specific proteins to analyze the level of expression and the integrity of a protein of interest. Another common application is in the Western blot technique where a protein lysate sample is separated on an SDS gel and the protein bands transferred onto a membrane. The membrane is incubated with a primary antibody that binds the protein of interest, and the the protein is detected using a secondary antibody conjugate that binds to the primary antibody. The secondary antibody is usually detectably labeled with an enzyme, but can also be labeled with probes such as fluorophores. Conjugating chelators to biomolecules is a relatively new technique that can be utilized in immunoassays. In U.S. Pat. No. 5,840,834, the inventors disclose joining two amino acid sequences with an electron acceptor moiety and a linking moiety.

Enzyme chelator conjugates, for example an HRP-NTA conjugate, have been prepared and been used for the detection of polyhistidine tagged proteins (U.S. Pat. No. 5,674,677). However, the conjugation method described is limited to enzymes that contain carbohydrate moieties that may be oxidized to produce reactive aldehyde groups. The NTA group is coupled to the enzyme via a Schiff base which is unstable unless reduced. The disadvantages of this technique are: (1) the lower efficiency of the conjugation reaction, (2) the need to reduce the Schiff base, which can compromise the activity of the enzyme and (3) requirement that the enzyme be a glycoproteins thereby limiting the types of biomolecules that can be modified.

The covalent attachment of chelators to biomolecules also offers a convenient tool to transport transition metal binding proteins/peptides to a target. An antibody bound to a polyhistidine sequence labeled with divalent metal ions such as nickel can be transported to specific cell receptors. Antibodies labeled with different chelators have been employed to transport radio-isotopes to a specific target for therapeutic purposes (U.S. Pat. No. 4,741,900, U.S. Pat. No. 5,756,685, US 2004/0156780).

A large number of procedures have traditionally been used to purify proteins, such as various chromatographic separations (by size, charge or affinity). Proteins that have been genetically modified to have a run of histidines (a histidine tag) can be purified on a nickel column (Hochuli et al. (1987), J. Chromat. 411:177-184; Porath (1992), Protein Exp. Purif. 2:263-281),and a number of commercial vendors provide systems for overexpressing and purifying such proteins. These tagged proteins can also be attached to substrates for manipulation, if desired.

There is no current method of coupling a chelator to a biomolecule which overcomes the disadvantages of the methods discussed above. There exists a need to simplify the procedure of detection, purification and transport of biomolecules such as proteins. The absence of a general method puts a substantial constraint on the usefulness of many molecules. It is apparent, therefore, that new methods for detecting, transporting and purifying biomolecules are greatly to be desired.

SUMMARY OF THE INVENTION

Accordingly, it is an object of the invention to provide a novel method of conjugating chelators to biomolecules. This methodology is useful for the detection, purification and transport of a wide range of biomolecules such as proteins, oligonucleotides, carbohydrates, and the like, and significantly simplifies other currently available techniques.

It is another object of this invention to provide novel compositions that can be used in these methods. The compositions include a conjugate comprising a binding moiety or a detectable moiety covalently linked to a chelating moiety via a crosslinking moiety.

In accomplishing these and other objectives, there has been provided, according to one aspect of the present invention, a compound having the general formula [Chel]-[linker]-X—CO—Ar-D, where [Chel] is a metal chelating moiety, [linker] is a substituted or unsubstituted ($C_{1-8}$)alkyl, X is O, NR, —NR—NR—, or S, Ar is substituted or unsubstituted ($C_{6-10}$)aryl or ($C_{5-10}$)heteroaryl; and D is selected from the group consisting of —CHO, —NRNR$^1$R$^2$, and —NH—N═CR$^1$R$^2$, where R, R$^1$ and R$^2$ are independently selected from hydrogen or substituted or unsubstituted ($C_{1-4}$)alkyl.

In accordance with another embodiment of the present invention, [Chel] is selected from the group consisting of nitrilotriacetic acid (NTA), iminodiacetic acid (IDA), bicinchoninic acid (BCA) and N,N,N'-tris(carboxymethyl)ethylenediamine (TED)

In accordance with yet another embodiment of the present invention, [Chel]-linker-X is nitrilotriacetic acid (NTA).

In accordance with another embodiment of the present invention, Ar is a substituted or unsubstituted phenyl or pyridine ring.

In accordance with another embodiment of the present invention, D is selected from —CHO, —NHNH$_2$ and —NH—N=CR$^1$R$^2$, where R$^1$ and R$^2$ are (C$_{1-4}$) alkyl.

In accordance with another embodiment of the present invention, there have been provided compounds having the formula:

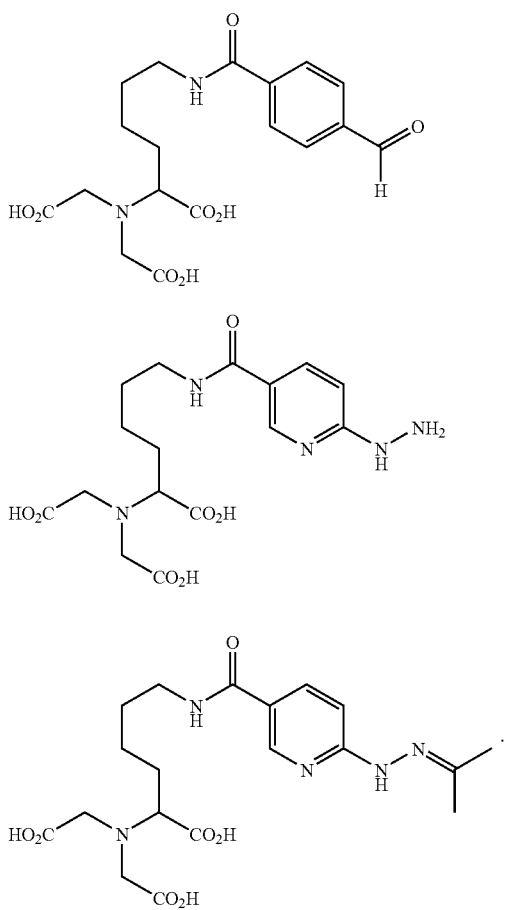

In accordance with another embodiment of the present invention, there has been provided, a conjugate having the structure: [Probe]-NH—CO—Ar$^1$-[hydrazone]-Ar$^2$—CO—NH-[chel], where [Probe] is a binding moiety or a detectable moiety, where each Ar$^1$ and Ar$^2$ independently are substituted or unsubstituted (C$_{6-10}$)aryl or (C$_{5-10}$)heteroaryl, where [hydrazone] is —C=N—NR— or —NR—N=C—, and where [Chel] is a metal chelating moiety. Ar$^1$ may be, for example, phenyl and Ar$^2$ may be pyridyl. In accordance with yet another embodiment of the present invention, Ar$^1$ may be pyridyl and Ar$^2$ may be phenyl.

In accordance with another embodiment of the present invention, [hydrazone] may be —C=N—NR—, or [hydrazone] may be —NR—N=C—.

In accordance with another embodiment of the present invention, [Probe] may be selected from the group consisting of binding moieties and detectable moieties. In another embodiment of the present invention, [Probe] may be a binding moiety selected from the group consisting of binding proteins and binding nucleic acids. In still another embodiment, [Probe] may be a binding moiety selected from the group consisting of streptavidin, avidin, biotin, green fluorescent protein, antibodies and antibody fragments. In another embodiment of the present invention, [Probe] may be a detectable moiety selected from the group consisting of horse radish peroxidase (HRP), alkaline phosphatase (AP), beta-galactosidase, nanoparticles and fluorophores such as Fluorescein, cy-3, cy-5 and derivatives thereof.

In accordance with another embodiment, [Chel] may be selected from the group consisting of nitrilotriacetic acid (NTA), iminodiacetic acid (IDA), bicinchoninic acid (BCA) and N,N,N'-tris(carboxymethyl)ethylenediamine (TED). [Chel] may be non-covalently bound to at least one metal atom.

In accordance with another embodiment of the present invention, any of the conjugates described above may further comprise a metal binding protein non-covalently bound to the metal atom.

In accordance with another aspect of the present invention, there has been provided a method of purifying a protein comprising a metal binding motif, comprising contacting a solution comprising the protein with a conjugate as provided above, where the probe is a binding moiety; contacting the resulting mixture with a matrix that specifically binds to the binding moiety, and eluting the protein from the matrix. Prior to eluting the protein, the matrix may be washed to remove impurities. In one embodiment, the binding moiety is streptavidin and the matrix comprises biotin linked to a solid support. In another embodiment, the binding moiety may be biotin and the matrix may comprise streptavidin linked to a solid support.

In accordance with another aspect of the present invention, there has been provided a method of detecting a protein comprising a metal binding motif, comprising contacting a sample suspected of containing the protein with the conjugate as described above, where the probe is a detectable moiety; and detecting the detectable moiety. In one embodiment the sample may be bound to a matrix. The matrix may be, for example, a membrane, a separation gel, or an ELISA plate.

The detectable moiety may, for example, be selected from a group consisting of horse radish peroxidase (HRP), alkaline phosphatase (AP), beta-galactosidase, nanoparticles and fluorophores such as Fluorescein, cy-3, cy-5 and derivatives thereof.

In accordance with another aspect of the present invention, there has been provided a method of transporting a protein comprising a metal binding motif to a target, comprising contacting the protein with the conjugate as described above to form a binding conjugate, where the probe is a binding moiety that specifically binds to the target, and contacting the resulting binding conjugate with the target. The binding moiety may be, for example, an antibody or antibody fragment, or a ligand specific for the target. The target may be, for example, a cell surface molecule.

In any of the embodiments described above, the metal binding motif may comprise a polyhistidine tag, typically containing at least 3 and up to 6 or more histidines.

In accordance with another embodiment of the present invention, the enzyme conjugate is selected from a group consisting of HRP-Ni$^{2+}$, alkaline phosphatase-Ni$^{2+}$ and βGal-Ni$^{2+}$ of fluorophore-Ni$^{2+}$ (RPE-Ni$^{2+}$; nanoparticle-Ni$^{2+}$).

Other objects, features, and advantages of the present invention will become apparent from the following detailed description. It should be understood, however, that the detailed description and the specific examples, while indicating preferred embodiments of the present invention, are given by way of illustration only, since various changes and modifications within the spirit and scope of the invention will become apparent to those skilled in the art from the detailed description.

DETAILED DESCRIPTION OF THE INVENTION

Figure 1:
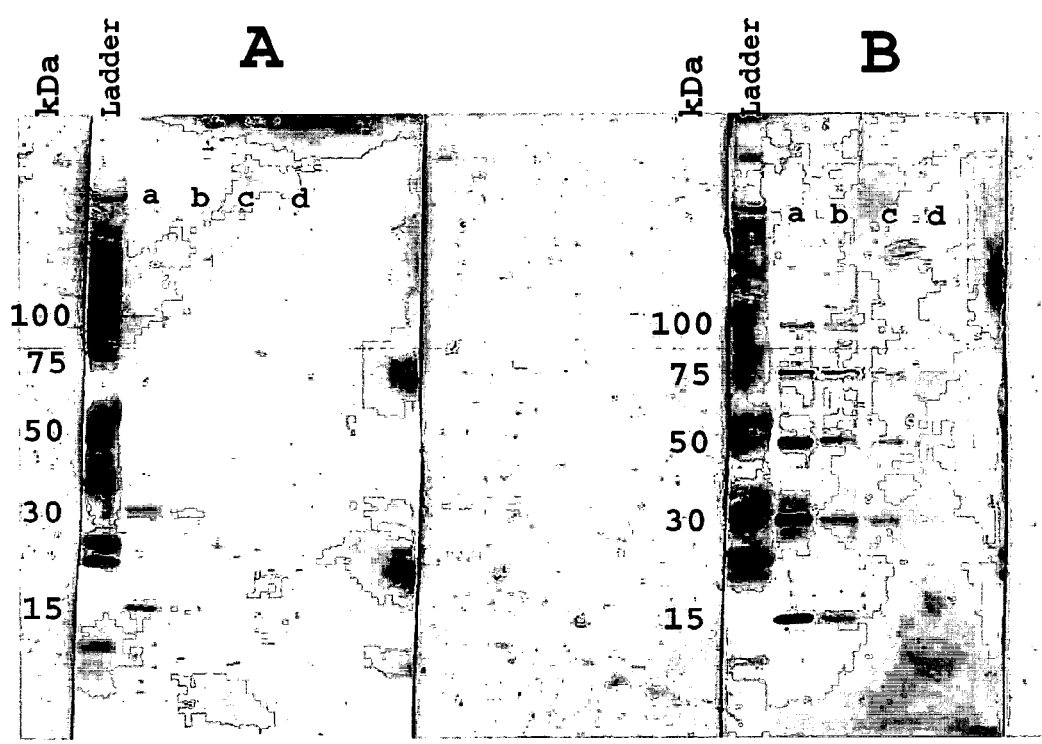
FIG. 1 shows the detection of His-tagged proteins using Rabbit anti-Goat IgG (pane A) or the nickel-NTA labeled form of Rabbit anti-Goat IgG (panel B) in conjunction with HRP-IgG (Horse Radish Peroxidase-Goat anti-rabbit IgG) conjugate.

Compositions and methods for purifying, detecting and transporting proteins or other macromolecules are provided. The compositions and methods are suitable for use with essentially any protein, macromolecule, or other moiety that contains a metal-binding motif. The compositions can be used to non-covalently link the protein, macromolecule, or other moiety to a probe molecule for detection, purification, transport, or other application. The methods are quick, efficient, easy to perform, and are of general applicability. For the sake of simplicity, the discussion below refers to proteins containing a metal binding motif, however the skilled artisan will recognize that the discussion also could refer to other macromolecules, such as nucleic acids, and other moieties, such as nanoparticles, unless otherwise specifically indicated or unless the context of the discussion clearly is limited to proteins.

The methods use the ability of metal ions, and particularly transition metal ions, to simultaneously coordinate with two different chelating moieties. The first chelating moiety is linked to the protein, while the second chelating moiety is bound to the probe molecule. Simultaneous coordination of the first and second chelating moieties to the metal ion links the probe to the protein, and allows detection, purification, transport, etc. of the protein via the probe molecule. Specific applications are discussed in more detail below but the skilled artisan will recognize that these applications are illustrative and not limiting.

The invention provides compositions comprising a metal chelator that can be linked to a probe moiety via a hydrazone linkage. The hydrazone linkage is readily formed in aqueous solution and is stable without further chemical transformation, making it particularly suitable for use with proteins, nucleic acids, and the like. Molecules are provided having the formula I:

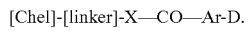

[Chel]-[linker]-X—CO—Ar-D.          I

In this molecule [Chel] is a metal chelating moiety, [linker] is a substituted or unsubstituted ($C_{1-8}$)alkyl, X is O, NR, —NR—NR—, or S, Ar is substituted or unsubstituted ($C_{6-10}$)aryl or ($C_{5-10}$)heteroaryl, and D is selected from the group consisting of —CHO, —NRNR$^1$R$^2$, and —NH—N=CR$^1$R$^2$, where R, R$^1$ and R$^2$ are independently selected from hydrogen or substituted or unsubstituted ($C_{1-4}$)alkyl The moiety D is used to form the hydrazone linkage discussed above. [Chel] may be, for example, nitrilotriacetic acid (NTA), iminodiacetic acid (IDA), bicinchoninic acid (BCA) N,N,N'-tris(carboxymethyl)ethylenediamine (TED), although the skilled artisan will recognize that other chelating moieties could be used. Advantageously, [Chel] is NTA. Ar may be a substituted or unsubstituted phenyl or pyridine ring. D may be, for example, —CHO (which is coupled to a hydrazine to form the hydrazone linkage), —NHNH$_2$ (which is coupled to an aldehyde to form the hydrazone linkage)and —NH—N=CR$^1$R$^2$ (which is a protected form of the hydrazine). R$^1$ and R$^2$ may be ($C_{1-4}$) alkyl.

Particular examples of these molecules include, but are not limited to A, B or C:

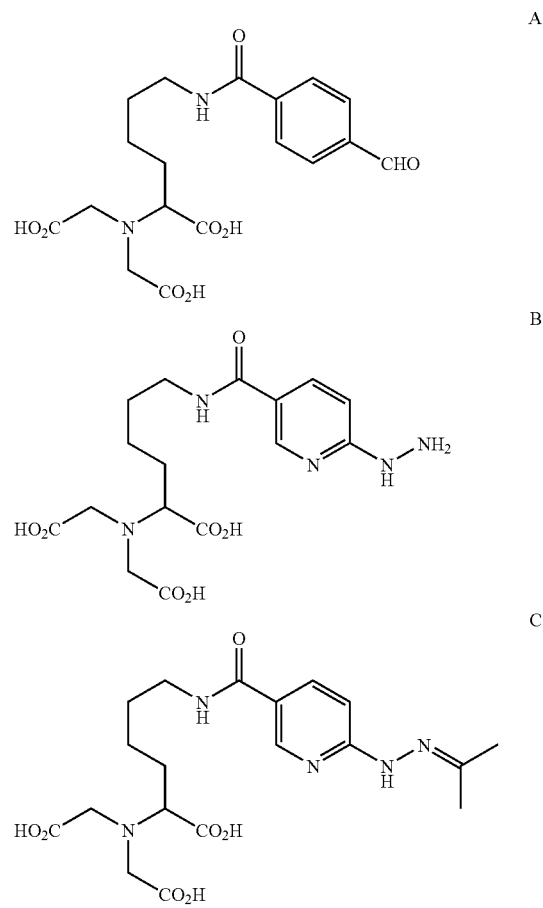

These molecules are covalently coupled to a probe moiety via the hydrazone linkage. Advantageously, the resulting molecule can be represented by the formula II:

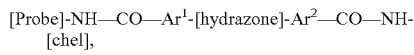

[Probe]-NH—CO—Ar$^1$-[hydrazone]-Ar$^2$—CO—NH-[chel],          II in which [Probe] is a binding moiety or a detectable moiety, each $Ar^1$ and $Ar^2$ independently is substituted or unsubstituted $(C_{6-10})$aryl or $(C_{5-10})$heteroaryl, [hydrazone] is —C=N—NR— or —NR—N=C—, and [Chel] is a metal chelating moiety. In specific embodiments, $Ar^1$ is phenyl and $Ar^2$ is pyridyl, or $Ar^1$ is pyridyl and $Ar^2$ is phenyl. The [Probe] moiety may be any moiety that is desired to be coupled to the [chel] moiety, but advantageously is selected from the group consisting of binding moieties and detectable moieties. Binding moieties include, but are not limited to binding proteins and binding nucleic acids. Suitable binding moieties include streptavidin, avidin, biotin, green fluorescent protein, antibodies and antibody fragments. Suitable detectable moieties include horseradish peroxidase (HRP), alkaline phosphatase (AP), beta-galactosidase, nanoparticles and fluorophores such as Fluorescein, cy-3, cy-5 and derivatives thereof.

Compounds of formula II can be bound to at least one metal atom via the [chel] moiety, and can be used to form complexes in which a metal binding moiety is non-covalently bound to the metal atom. Suitable metal binding moieties include, but are not limited to proteins containing metal binding motifs such as a polyhistidine tract.

The compositions described above can be used in a method of purifying a protein comprising a metal binding motif. In this method, a solution containing the protein is contacted with a conjugate of formula II, in the presence of a metal ion. In this instance the probe is a binding moiety. The resulting complex is isolated by contacting the solution mixture with a matrix that specifically binds to the binding moiety, and then eluting the protein of interest from the matrix using a suitable buffer containing a metal chelating composition. Prior to eluting the protein, the matrix is washed to remove impurities. The skilled artisan will be aware that a wide variety of binding pairs can be used in this method. For example, the streptavidin/biotin binding pair can be used such that the binding moiety is streptavidin and the matrix contains biotin linked to a solid support, or vice versa.

The compositions described above also can be used in a method of detecting a protein comprising a metal binding motif. In this method, a sample containing the protein is contacted with a conjugate of formula II in the presence of a metal ion. In this example, the probe is a detectable moiety. This method can be used, for example, where the sample is bound to a matrix, such as a membrane, separation gel, or an ELISA plate. The detectable moiety can be any of a wide variety of, for example, detectable labels that are well known in the art, such as horseradish peroxidase (HRP), alkaline phosphatase (AP), beta-galactosidase, nanoparticles, or fluorophores such as Fluorescein, cy-3, cy-5 and derivatives thereof.

The compositions described above also can be used in a method of transporting a protein containing a metal binding motif to a target. In this method, a protein is contacted with a conjugate of formula II in the presence of a metal ion to form a binding conjugate. In this instance the probe is a binding moiety that specifically binds to the desired target. The resulting binding conjugate is then used to contact a sample containing the target. The binding moiety may be, for example an antibody or antibody fragment, or a ligand specific for the target. The target may be, for example, a cell surface molecule.

In all of the compositions and methods described above, the metal binding motif may contain a polyhistidine tag. Suitable polyhistidine tags comprise at least 3-6 histidines.

Definitions

As used herein, the term "alkyl" denotes either straight or branched chain groups for eg. methyl, ethyl, propyl, isopropyl, sec-butyl, etc.

As used herein, the term "aryl" denotes a phenyl radical or an ortho-fused bicyclic carbocyclic radical having about nine to ten ring atoms in which at least one ring is aromatic.

As used herein, the term "heteroaryl" refers to a radical attached via a ring atom of a monocyclic or bicyclic aromatic ring containing 5-14 ring atoms, such as a monocyclic ring containing from 5-6 ring atoms, comprising carbon and one, two, three or four heteroatoms including, for example, non-peroxide oxy (—O—), thio (—S—), sulfinyl (—SO—), sulfonyl (—S(O)$_2$—), amine —N—, —N(O)—, —N=, etc. Bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, pteridine, purine, carbazole, acridine and the like. Preferred heteroaryl groups include imidazolyl, triazolyl, triazinyl, oxazoyl, isoxazoyl, thiazolyl, isothiazoyl, thiodiazolyl, pyrrolyl, pyrazolyl, pyrazinyl, tetrazolyl, pyridinyl, pyrimidinyl, indolyl, isoquinolyl, quinolyl and the like.

Preparation of the chelator-cross linker complex

In the first step, an organic chelator, such as nitrilotriacetic acid (NTA), iminodiacetic acid (IDA), bicinchoninic acid (BCA) or N,N,N'-tris(carboxymethyl)ethylenediamine (TED), is coupled with a cross linking agent such as succinimidyl 4-formylbenzoate (SFB) or succinimidyl 6-hydrazinopyrinine acetone hydrazone (SANH) as depicted in scheme 1. Generally an aqueous solution of the chelator is added to a solution of the cross linking agent in DMSO containing triethyl amine (TEA) such that the ratio of water:TEA by volume is in the range of 1:1 to 5:1 and the ratio of water:DMSO:TEA by volume is in the range of 1:1:1 to 5:5:1. After stirring the mixture overnight at room temperature, it can be used in the next step without any further purification.

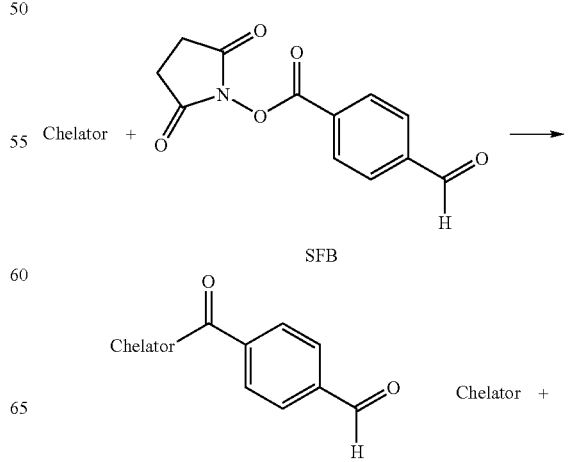

Scheme 1

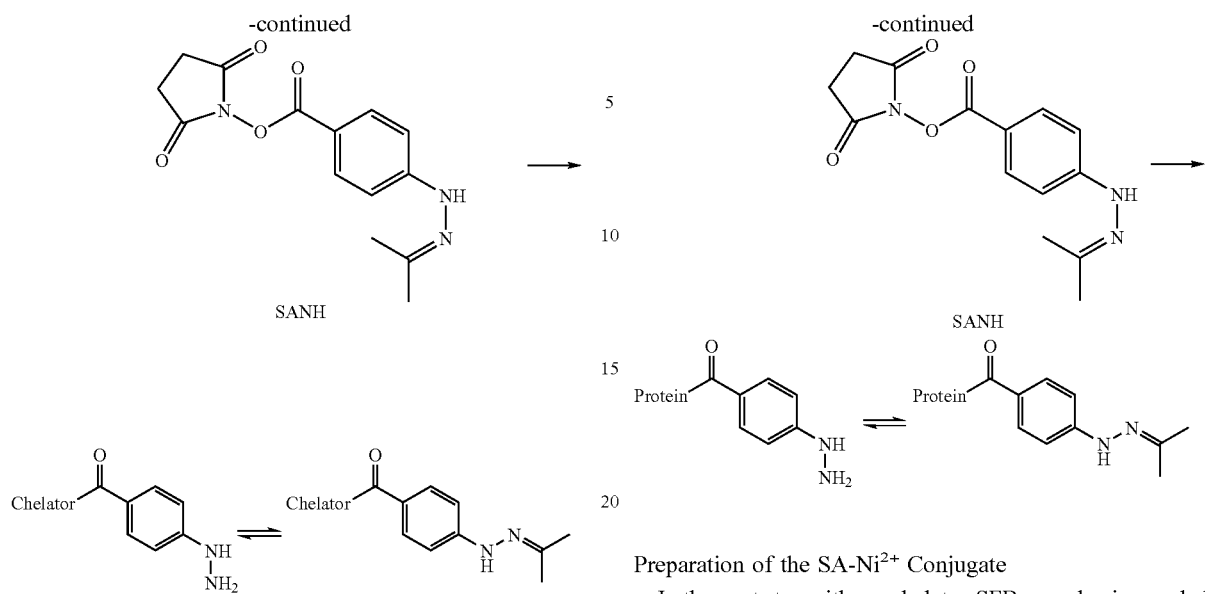

SANH

Preparation of the Protein-Cross Linker Complex

In the second step, a protein such as streptavidin, horse radish peroxidase (HRP), alkaline peroxidase (AP) or an antibody which has been previously purified by dialysis is coupled with a cross linking agent such as succinimidyl 4-formylbenzoate (SFB) or succinimidyl 6-hydrazinopyrinine acetone hydrazone (SANH) as depicted in scheme 2. Generally, a solution of the cross linker in DMSO is added to the protein so as to get a molar ratio of cross linker:protein in the range of 20:1 to 40:1 in DMSO. Under gentle agitation, the mixture is incubated for 1-6 hours at room temperature or overnight at 2-6° C. The resulting incubated mixture can be used in the next step without further purification.

Preparation of the SA-Ni$^{2+}$ Conjugate

In the next step, either a chelator-SFB complex is coupled to a protein-SANH complex or a chelator-SANH complex is coupled to a protein-SFB complex as depicted in schemes 3 and 4. Upon incubation with gentle stirring, the aldehyde group of the SFB complex reacts with the hydrazine moiety of the SANH complex to form the corresponding hydrazone and links the two complexes together. Typically, the coupling is carried out in a buffer solution with a pH range 4.5 to 6.5 and the incubation is carried out for 2 hours—overnight between room temperature and 2° C. The resulting mixture is subjected to a series of dialyses beginning with water (2-3 times) followed by 5-25% glycerol/TBS buffer (1-2 times).

The dialyzed mixture is then treated with an excess of NiSO$_4$ as a 10-30% solution in glycerol/water and stirred for 1-4 hours. The unreacted NiSO$_4$ is removed from the resulting SA-Ni$^{2+}$ conjugate by means of dialysis overnight using a 10-30% glycerol/TBS buffer.

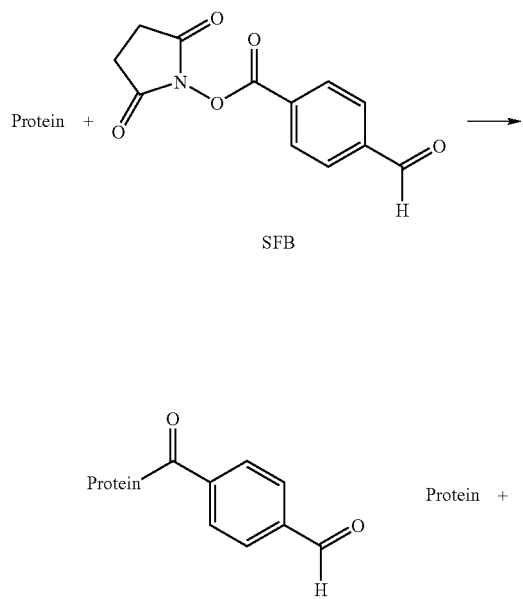

Scheme 2

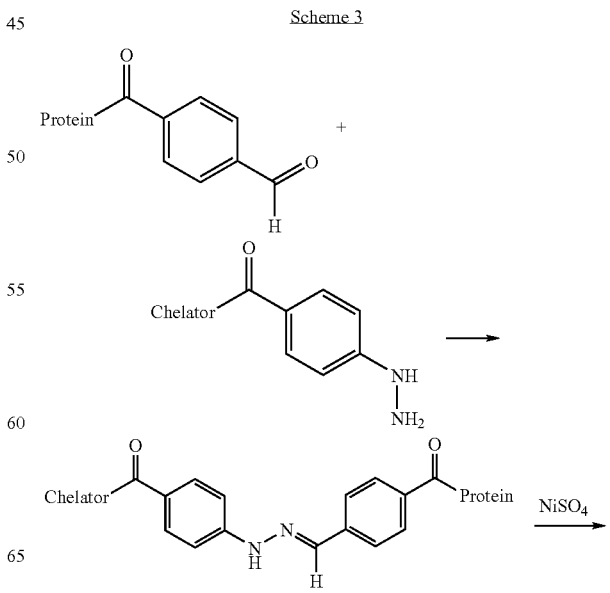

Scheme 3

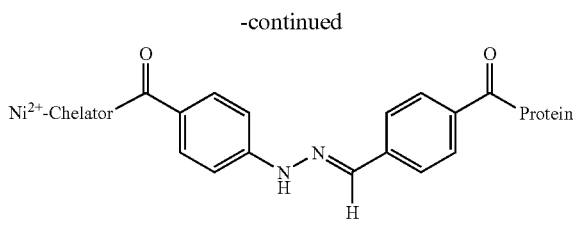

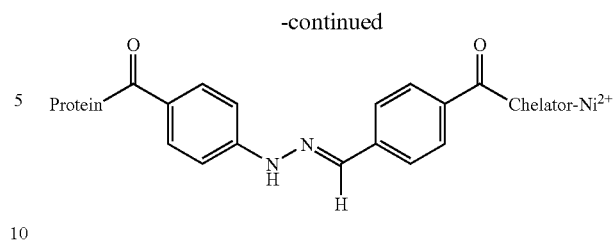

Scheme 4

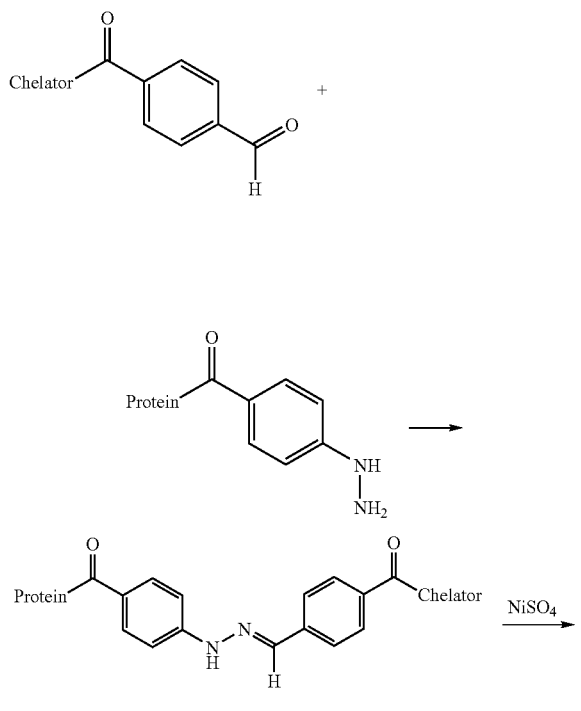

Purification of a Histidine-Tagged Recombinant Protein Using the SA-Ni$^{2+}$ Conjugate The histidine-tagged protein is over expressed in a preferred host cell such as *E. coli*. The cells are then lysed in presence of a 5-25 mM imidazole solution so as to minimize non-specific binding in the subsequent steps. A denaturant such as 5-10M Urea is added to the lysate mixture to expose the histidine tag and enhance the interaction with the SA-Ni$^{2+}$ conjugate. The SA-Ni$^{2+}$ conjugate is then added to the lysate mixture and incubated for 1-4 hours at a temperature ranging from 2° C. to room temperature with gentle stirring (schemes 5 and 6).

A column containing a matrix that selectively binds to the SA-Ni$^{2+}$-protein(polyhistidine) complex is prepared. Typically, biotin such as magnetic bead biotin can be employed as the matrix. The complex is loaded onto the column and washed multiple times with 2-3 column volumes of 5-10M Urea to remove the host cell contaminants. Following these washes, a buffer containing appropriate amount of imidazole is eluted. Generally, a 100-500 mM imidazole solution can be employed. The polyhistidine tagged protein that is eluted is collected and subjected to further purification.

SDS-PAGE chromatography is employed to determine the purity and integrity of the purified protein. Subsequent dialysis using an appropriate buffer solution results in a purified protein that is stored in the appropriate storage buffer.

The used column is regenerated by charging it with a buffer containing free biotin. This results in the elution of the protein-NTA complex. Alternatively, the used column can be charged with a buffer containing NiSO$_4$. This results in recharging the NTA moieties bound on the matrix via a protein-biotin interaction.

Scheme 5

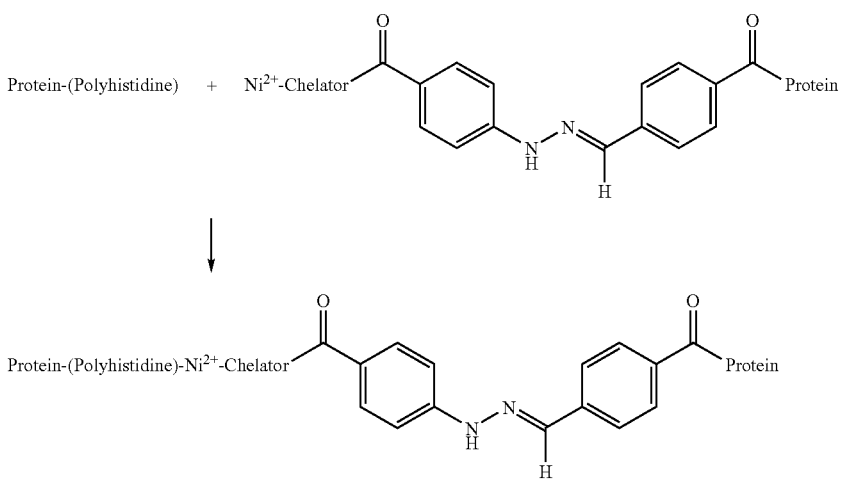

-continued
Scheme 6

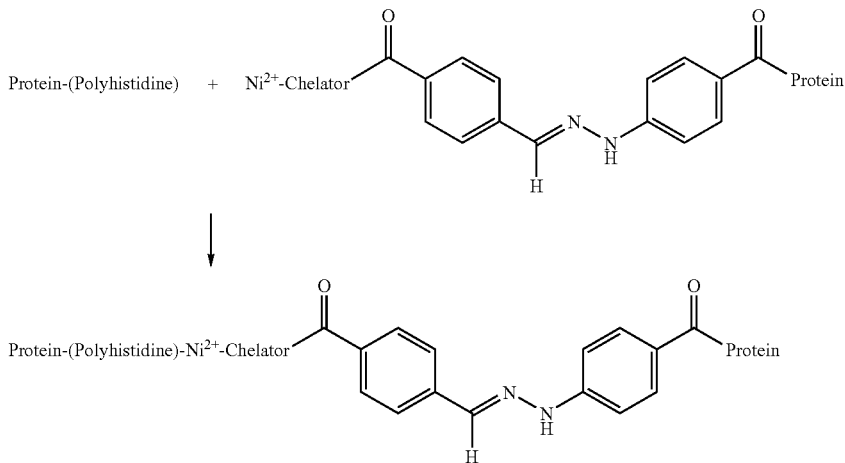

Scheme 6

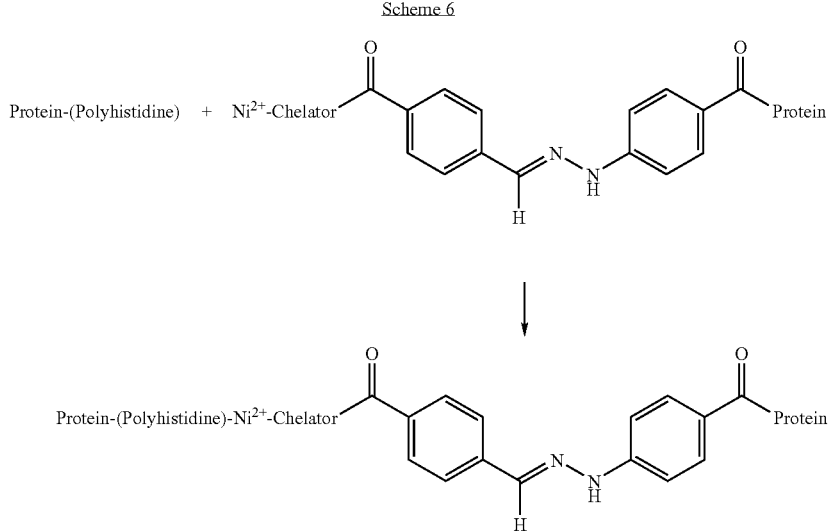

Detection of a Histidine-Tagged Recombinant Protein Bound to the SA-$Ni^{2+}$ Conjugate Several well known analytical tools and techniques available to one skilled in the art, can be employed for detection of a histidine-tagged recombinant protein bound to the SA-$Ni^{2+}$ conjugate. SDS-Page Chromatography, Ultraviolet-visible (UV-Vis) spectroscopy and western blotting, enzyme linked immunosorbent assay (ELISA) are particularly suited for this invention. His-tagged protein detection techniques using Horseradish-$Ni^{2+}$, Alkaline Phosphatase-$Ni^{2+}$, βGal-$Ni^{2+}$ of fluorophore-$Ni^{2+}$ (RPE-$Ni^{2+}$; nanoparticle-$Ni^{2+}$) that can be employed to detect His-tagged proteins are described in U.S. Pat. No. 5,674,677 and are herein incorporated by reference.

Transport of a Histidine-Tagged Recombinant Protein Using Antibody-$Ni^{2+}$ Conjugates A histidine-tagged protein of therapeutic value is incubated with an antibody-$Ni^{2+}$ conjugate for 1-4 hours at a temperature ranging from 2° C. to room temperature with gentle stirring. The resulting binding conjugate is transported to a cell receptor target such as cancer cells that are specific to that particular antibody. This methodology delivers therapeutic proteins linked to an antibody-$Ni^{2+}$ conjugate via a polyhistidine tag without compromising the antibody-antigen interaction.

Synthesis of NTA-CM-Lysine-SFB or NTA-CM-Lysine-SANH 15 mg of CM-lysine was dissolved in 400 μL of water. 530 μL of DMSO followed by. 105 μL of triethylamine (TEA) were added subsequently and the mixture was stirred thoroughly. 1 mg of SFB or SANH was then added and the solution was incubated for 1-2 hours at ambient temperature with gentle mixing. The resulting NTA-CM-lysine-SFB or NTA-CM-lysine-SANH was used in the next step without further purification.

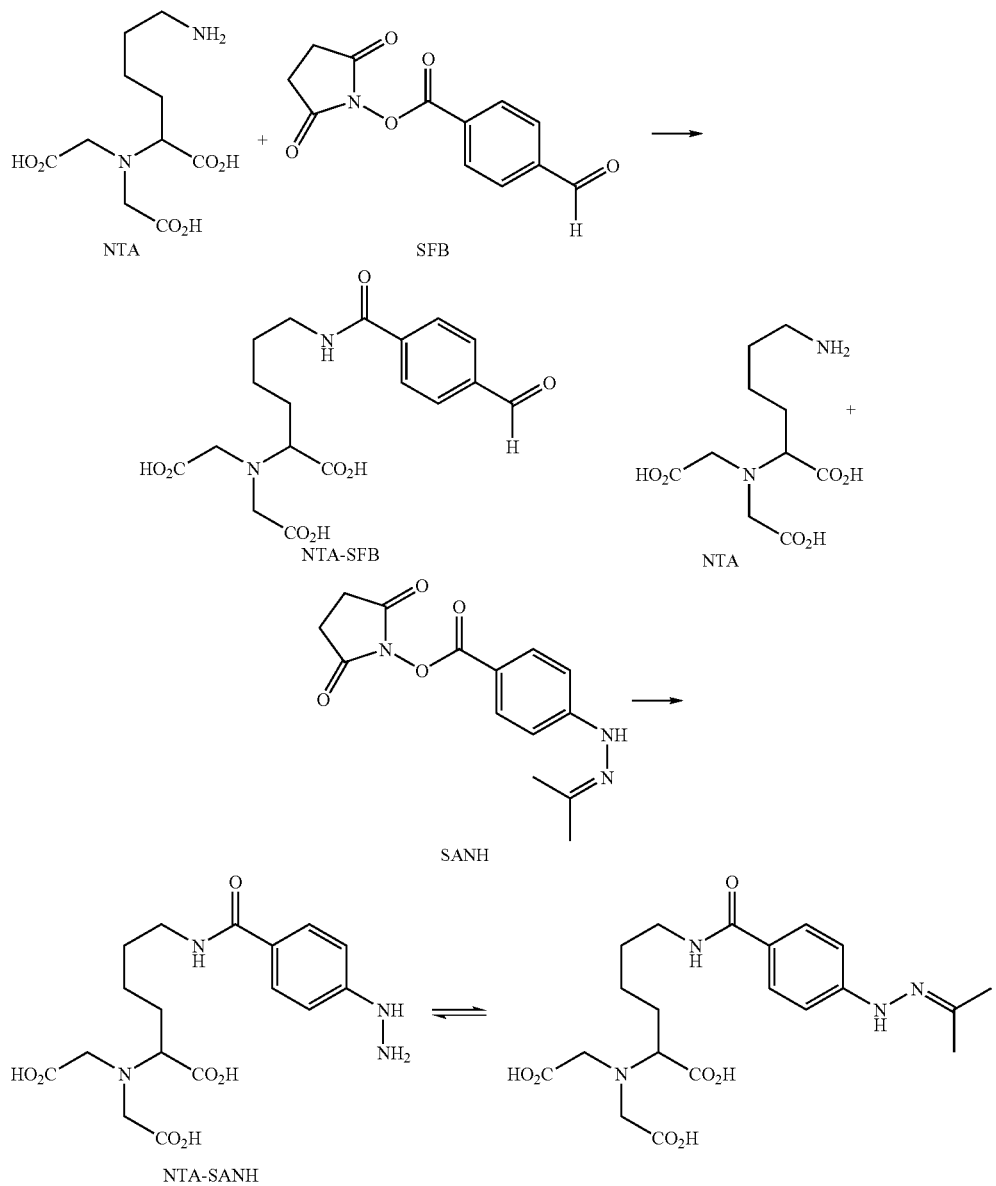

Synthesis of Streptavidin-SFB or Streptavidin-SANH

A sample of streptavidin was subjected to dialysis using a 0.1M sodium phosphate buffer at pH 7.2 in 0.15M NaCl so that the amount of streptavidin to buffer was about 1 to 5 mg/mL. Either SFB or SANH was dissolved in DMSO and added to the dialyzed protein with gentle mixing at a 1 to 50 fold molar excess of the protein. Incubation for 1-2 hours at ambient temperature or overnight at 4° C. resulted in the corresponding streptavidin-SFB or streptavidin-SANH complex respectively. The unreacted cross linker was removed either by dialysis or by loading the mixture on a desalting column and eluting with 0.1M citric/citrate buffer at pH 6.0 in 0.15M NaCl.

Synthesis of the SA-Ni$^{2+}$ Conjugate

The NTA-CM-lysine-SFB complex is mixed with the streptavidin-SANH complex or the NTA-CM-lysine-SANH complex is mixed with the streptavidin-SFB complex with gentle stirring. The molar ratio of the chelator-crosslinker to protein-crosslinker is maintained at 1:5. The mixture is incubated for 1-2 hours at ambient temperature or overnight at 4° C. The resulting mixture is subjected to a series of dialyses beginning with water (2-3 times) followed by 5-25% glycerol/TBS buffer (1-2 times).

The dialyzed mixture is then treated with an excess of NiSO$_4$ as a 10-30% solution in glycerol/water and stirred for 1-4 hours. The unreacted NiSO$_4$ is removed from the resulting SA-Ni$^{2+}$ conjugate by means of dialysis overnight using a 10-30% glycerol/TBS buffer.

Purification of a Histidine Tagged Protein with the SA-Ni$^{2+}$ Conjugate

A (His)$_6$ tagged protein is overexpressed in E. coli host cells. The cells are lysed in the presence of 15 mM imidazole. 7M urea is added to the lysate mixture to expose the (His)$_6$ tag and enhance the interaction with the SA-Ni$^{2+}$ conjugate. The SA-Ni$^{2+}$ conjugate is added to the lysate and the mixture is gently stirred and incubated for 2 hours at 4°

C. A magnetic bead biotin column is prepared and the protein-(His)$_6$-SA-Ni$^{2+}$ sample is loaded onto the column.

The column is then washed with 7M urea (4-5 column volumes) in the presence of 15 mM imidazole to remove hoat cell contaminants. A buffer containing 250 mM imidazole is then employed to elute the (His)$_6$ tagged protein. SDS-PAGE chromatography is performed to determine the purity and integrity of the protein. The column is regenerated either by eluting the bound streptavidin-NTA using a buffer containing free biotin or by recharging the NTA moieties by washing with a buffer containing NiSO$_4$.

EXAMPLES

The following examples are included for illustrative purposes only and are not intended to limit the scope of the invention.

Example 1

Detection of Polyhistidine Containing Proteins on a Nitrocellulose Membrane.

SDS PAGE and Western Blotting

FIG. 1 shows the detection of His-tagged proteins (polyhistidine -containing protein markers from Qiagen Corp., Cat # 34705) using Rabbit anti-Goat IgG (pane A) or the nickel-NTA labeled form of Rabbit anti-Goat IgG (panel B) of the invention in conjunction with HRP-IgG (Horse Radish Peroxidase-Goat anti-rabbit IgG) conjugate. The protein mix was resolved over a 4%-20% SDS denaturing protein gel and the protein bands were transferred onto a nitrocellulose membrane. The rabbit anti-Goat IgG (panel A) or the nickel-NTA labeled form of rabbit anti-Goat IgG (panel B) were maintained at 10 µg/20 mL. The HRP Goat anti-Rabbit IgG conjugate was maintained at 20 µg/20 mL for each condition. Lanes a, b, c, and d indicate four different amounts of the five His-tagged protein bands: 50-75 ng, 10-15 ng, 2-3 ng and 0.4-0.6 ng, respectively. The proteins corresponding molecular weight is denoted in kDa.

Description of the Assay

The protein mixes were fractionated over SDS-PAGE gel and the protein bands were transferred onto nitrocellulose membrane using standard Western Blotting protocol. The membranes were blocked with 1× detector block solution (KPL; Cat # 71-83-00) for one hour. After the blocking the appropriate amount of the IgG or Ni$^{2+}$-IgG was added directly to the detector block solution and the membrane was incubated for 1 hour with gentle agitation. Following washes (3 times) with TBST buffer (Tween containing Tris borate saline buffer) for 5 min each, the membranes were incubated in the presence of the HRP Goat anti-Rabbit IgG conjugate in 1% BSA/TBST, for 1 hour with gentle agitation. Following washes, the His-tagged protein bands were detected using a chromogenic HRP substrate, TMB (KPL; Cat # 50-77-00).

Results and Conclusion

Each of the His-tagged protein was detected, panel B lanes a and b, compared to the control (see panel A) suggesting that the Ni$^{2+}$-IgG conjugate effectively interacted with the poly-His motif—without significantly compromising the interaction between the Gt anti-Rabbit antibody and the Ni$^{2+}$-IgG. The obvious inference from this result is that Ni$^{2+}$-NTA-IgG conjugates could be invaluable biological tools for transporting poly-His containing proteins or peptide to specific cellular receptor targets. Antibody-Ni$^{2+}$ conjugates could be a plausible substitute for bi-affinity antibodies for screening the level of efficacy of protein drugs—circumventing the need to clone and express antibody molecules that binds to 2 different antigens or to chemically conjugate precious proteins to an antibody. In addition, a single preparation of Ab-Ni$^{2+}$ that is specific to a cell receptor has a potential of becoming a more universal transporting biomolecule that would significantly enhance the specificity of protein drugs, by taking advantage of the strong and specific interaction between divalent metal cations and polyhistidine sequences.

Example 2

Detection of Goat IgG on a Nitrocellulose Membrane.

SDS PAGE and Western Blotting

Figure 2:
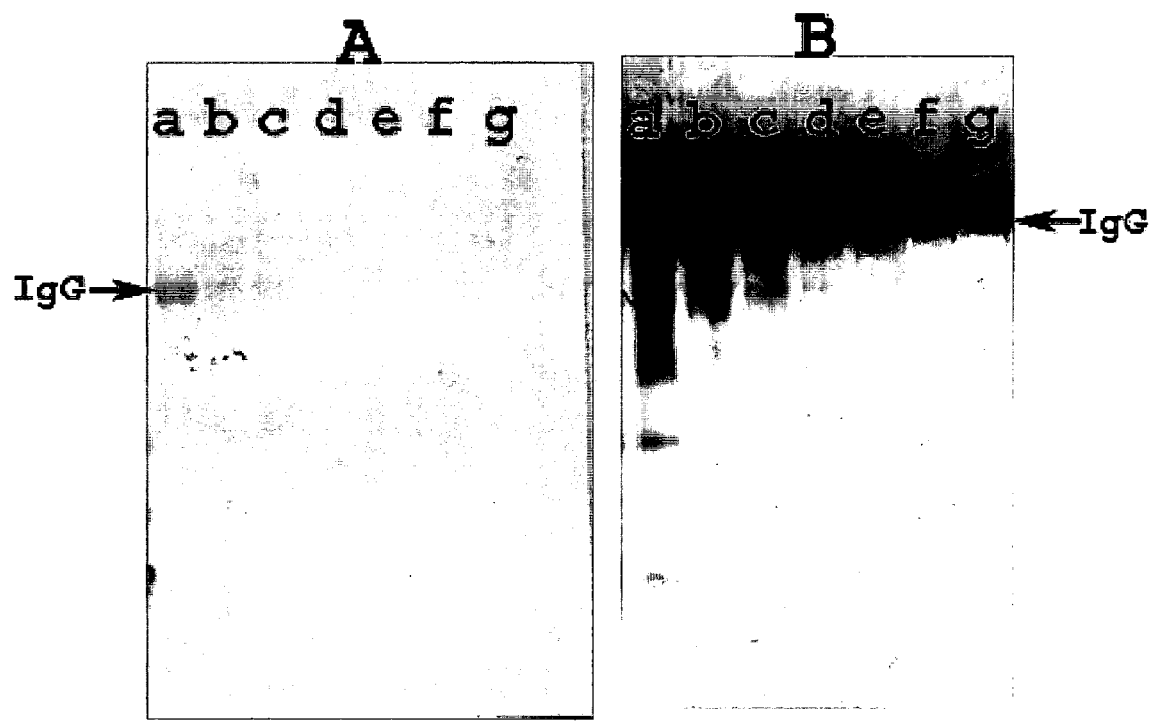
FIG. 2 shows the detection of Goat IgG using a Western Blotting assay IgG-Ni conjugate.

FIG. 2 shows the detection of Goat IgG using a Western Blotting assay IgG-Ni conjugate of the invention. Following the fractionation of the IgG samples over a 4%-20% SDS denaturing protein gel, the protein bands were transferred onto a nitrocellulose membrane. Panels A and B represent membranes that were detected using Ni$^{2+}$-NTA Rabbit anti-Goat IgG conjugate in conjugation with a His-tagged β-gal or HRP-Gt anti-Rt IgG conjugate, respectively. In each panel, the lanes a, b, c, d, e, f, and g represent a series of dilutions of the fractionated Goat IgG: 1 µg, 200 ng, 40 ng, 8 ng, 1.6 ng, 0.32 ng and 64 pg, respectively. The concentration of the Ni-IgG was maintained at 5 µg/10 mL for each condition, whereas the His-tagged β-gal and the HRP-anti-Rt-IgG were maintained at 200 µg/10 mL and 2 µg/10 mL, respectively.

Description of the Assay

The IgG samples were fractionated over SDS-PAGE gel and were transferred onto nitrocellulose membrane using standard Western Blotting protocol. After blotting the membrane with 1% BSA/TBST solution for an hour, the Ni-IgG conjugate was added directly to the blocking mix and the membrane was incubated for 1 hour with gentle agitation. Following washes (3 times) with TBST buffer (Tween containing Tris borate saline buffer) for 5 min. each, the membranes were incubated in the presence of either His-tagged β-gal (panel A), wild-type β-gal (data not shown) or HRP Rabbit anti-Goat IgG conjugate (panel B) in 1% BSA/TBST for 1 hour with gentle agitation. Following washes, the IgG bands were detected using the enzyme substrate HistoMark® X-GAL (KPL; Cat 54-13-00) for the β-gal or TMB for the HRP-IgG incubation.

Results and Conclusion

The detection of the Goat IgG bands with the His-tagged β-gal as shown on panel A (lanes a, b, and c), albeit at a lower efficiency compared to the detection with the HRP-IgG (panel B), suggests that the Ni-IgG biomolecule interacts with the antigen on the membrane in addition to the His-tagged fusion. However, no level of IgG detection was observed when the wild-type β-gal protein was used (data not shown) implying that the interaction of the Ni-NTA with the poly-His fusion is required for the β-gal to be retained on the membrane. In summary these results show that the Rabbit Ni-NTA-anti Goat IgG efficiently interacts with i) the Gt IgG antigen on the membrane (panels A and B) ii) the Goat anti-Rt IgG conjugated to the HRP (panel B) and iii) the His-tag motif of the recombinant β-gal (panel A). From these data, one can infer that the covalent attachment of Ni-NTA onto IgG does not significantly compromise the antibody-antigen interaction.

Example 3

Direct Detection of BLV-1 (His)$_6$ on a Nitrocellulose Membrane

Figure 3:
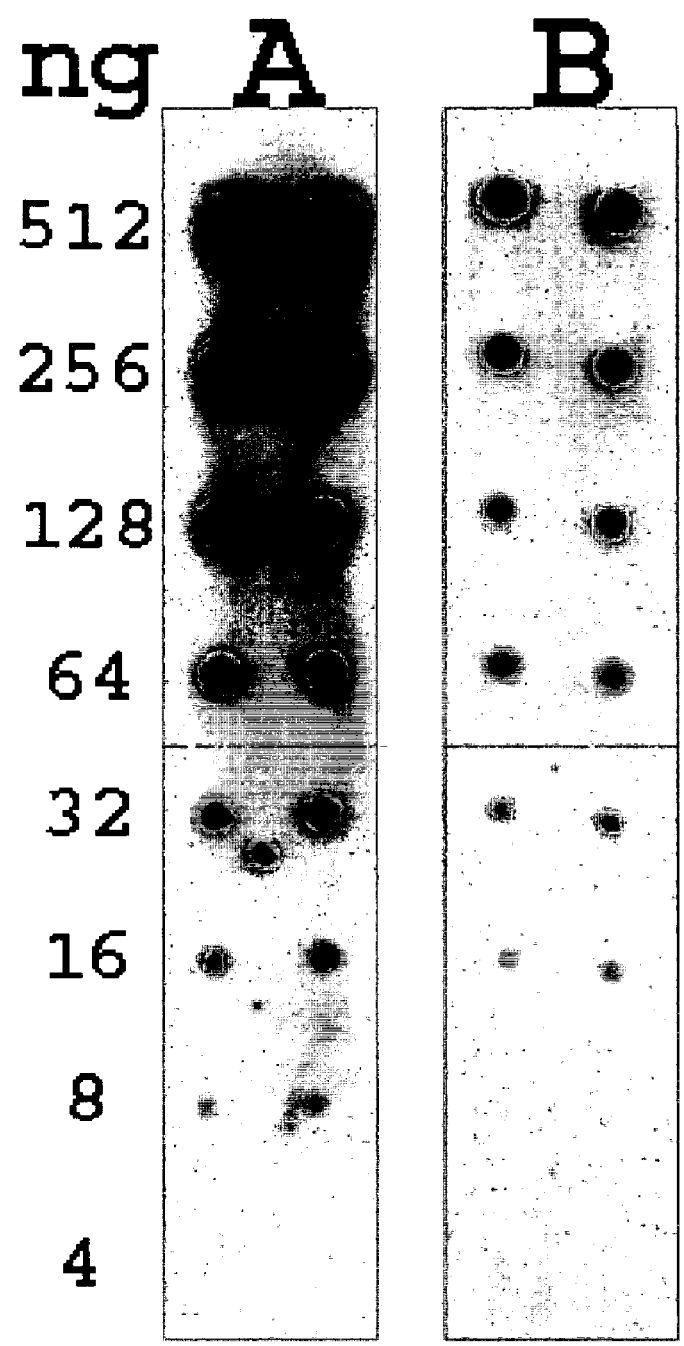
FIG. 3 shows the detection of BLV-1 (His)$_6$ (Bovine Leukemia Virus-1 core protein containing a 6-histidine motif) in a dot blotting assay with enzyme conjugates.

Dot Blotting:

FIG. 3 shows the detection of BLV-1 (His)$_6$ (Bovine Leukemia Virus-1 core protein) in a dot blotting assay with enzyme conjugates of the invention. The *E. coli* strain containing the over-expression plasmid (pQE) containing the nucleotide sequence of the segment of the core protein of BLV-1 was a gift from Dr. Darrell L Peterson (Virginia Commonwealth university). The gene was derived by reverse transcribing (RT-PCR) infected cells. The BLV-1 was over-expressed and was purified in a single step over a Ni-NTA column purchased from Qiagen. The BLV-1 samples diluted in TBS buffer were spotted in duplicate, in two-fold dilution from top to bottom, starting at 512 ng. The protein spots were detected using AP-Ni$^{2+}$ (panel A) or HRP-Ni$^{2+}$ (panel B) conjugate, respectively. Each of the enzyme-Ni$^{2+}$ conjugate was maintained at 1 µg/5 mL.

Description of the Assay.

The BLV-1 samples were spotted onto a nitrocellulose membrane (1 µL per spot) and the membrane was allowed to dry by air for 3 hours. The membrane was blocked in either detector block solution or detector block solution (AP-Ni$^{2+}$) that contains 0.2% detector block powder (HRP-Ni$^{2+}$) for an hour and the appropriate amount of enzyme-Ni conjugate was added directly to the block solution. Following incubation in the presence of Ni conjugate for 30 min. with gentle agitation, the conjugate mix was decanted. The membrane were then washed 3 times with TBST buffer (Tween containing Tris borate saline buffer), in addition the membrane shown panel A was washed 2 times for 2 min with phosphatase assay buffer (KPL; 50-63-14). The protein spots were detected using a chemiluminescent substrates either CDP-star (KPL; Cat. # 50-60-05) in the presence of an enhancer (Tropix, Nitro-Block) for AP or LumiGLO (KPL; Cat. # 54-61-00) for HRP.

Results and Conclusion

The results shown in FIG. 3 suggest that the Ni-NTA-Enzyme conjugates prepared using the heterobifunctional cross-linkers (SANH and SFB) of this invention are proficient for the purpose of detecting polyhistidine containing proteins. Although the BLV-1 is not denatured and hence the His-tag portion may not have been as readily exposed, the conjugates efficiently detected in the low ng level.

Example 4

Detection of BLV-1 (His)$_6$ on a Nitrocellulose Membrane.

Dot Blotting

Figure 4:
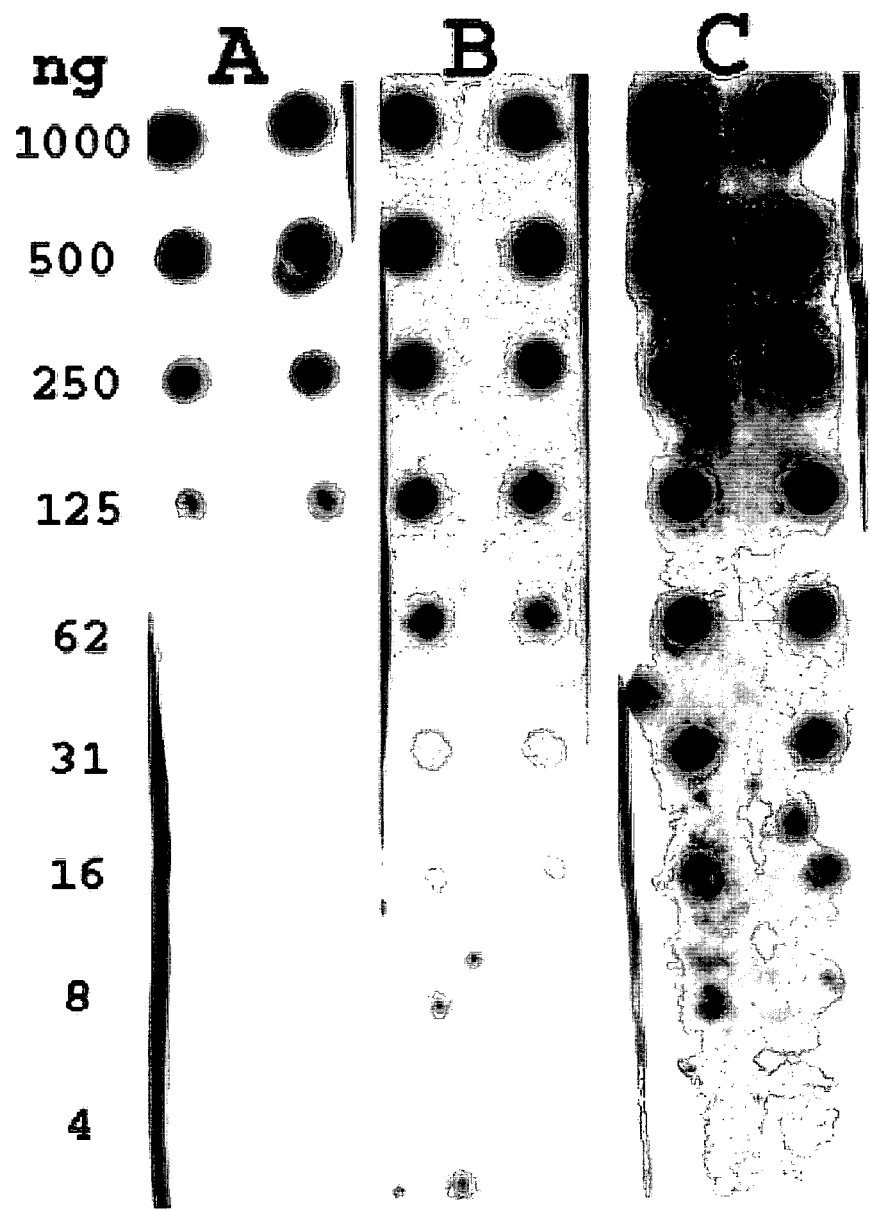
FIG. 4 shows the detection of BLV-1 (His)$_6$ in a dot blotting assay.

FIG. 4 shows the detection of BLV-1 (His)$_6$ in a dot blotting assay. The BLV-1 samples diluted in TBS buffer were spotted in duplicate, in two-fold dilution from top to bottom, starting at 512 ng. The protein spots were detected using AP-Ni (panel A) or streptavidin-Ni (SA-Ni) in conjunction with alkaline phosphatase-Biotin (panel B) or HRP-Ni (panel C). Each enzyme conjugate, AP-Ni, SA-Ni, AP-Biotin and HRP-Ni was maintained at 500 ng in 5 mL.

Description of the Assay.

The BLV-1 samples were spotted and blocking, incubation and detection steps are as described in example 3, with minor changes. For panel B, the block solution is 5 mL of detector block with 1% detector block powder. Following the incubation of the membrane with the respective Ni$^{2+}$ conjugate, the conjugate mix was decanted. For each detection condition, the membrane was washed 3 times with TBST in the presence of 1% BSA buffer for 5 min each and the protein spots were detected using either chemiluminescent substrates. However, the membrane shown in panel B was incubated in the presence of AP-Biotin in the wash mixture for 30 min. Following washes, the protein spots were finally detected with CDP-star in the presence of Nitro-Block enhancer.

Results and Conclusion

These results show that each Ni-NTA-conjugate of this invention prepared using the heterobifunctional cross linkers are proficient in interacting with polyhistidine containing proteins. Especially the efficient binding of the His-tag proteins with the streptavidin-Ni (SA-Ni) conjugate, without significantly comprising the biotin-streptavidin interaction, shows that SA-Ni is bi-affinity biomolecule. The obvious implication is that SA-Ni, a conjugate of this invention, can be used both as a His-tag detection reagent and its utility can also be extended for purifying recombinant proteins.

Example 5

Detection of Polyhistidine-Containing Proteins on a Nitrocellulose Membrane.

SDS PAGE and Western Blotting

Figure 5:
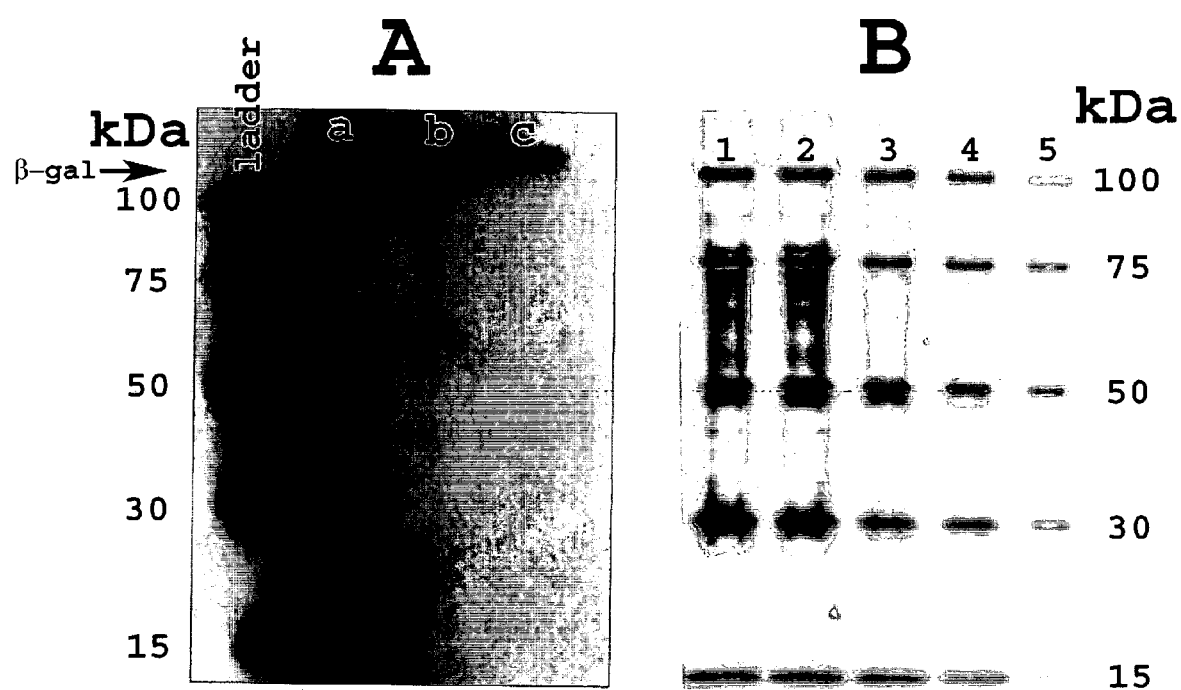
FIG. 5 shows the detection of His-tagged proteins with AP-Ni conjugate.

FIG. 5 shows the detection of his-tagged proteins with AP-Ni conjugate of this invention. FIG. 5A shows the detection of β-gal using AP chemiluminescent substrate, where lanes a, b, and c represent 1 µg, 0.5 µg and 0.25 µg, respectively. The ladder lane denotes a standard His-tag protein ladder purchased from Qiagen, with the respective kDa. FIG. 5B shows the detection of the 5 polyhistidine containing molecular weight marker proteins using AP chromogenic substrate, where lanes 1, 2, 3, 4, and 5 represent 25 ng, 6.2 ng, 1.6 ng, 0.4 ng and 0.1 ng, respectively. The protein mixes were resolved over a 4%-20% SDS denaturing protein gel (BioRad) and transferred onto a nitrocellulose membrane. The AP-Ni conjugate was maintained at 5 µg in 10 mL and 50 µg in 20 mL for panel A and B, respectively.

Description of the Assay.

The proteins were fractionated over SDS-PAGE gel and were transferred onto nitrocellulose membrane using standard western blotting protocol. Blocking membrane, incubating with conjugate, and detecting with the substrate is as described above.

Results and Conclusion

Each of the five His-tagged molecular weight marker and the β-gal bands were efficiently detected implying the strong interaction between the AP-Ni of this invention and the polyhistidine motif. Though there are only 10-15 lysine residues available for modification, alkaline phosphatase can be efficiently labeled with Ni-NTA. The inference from this is that the labeling methodology described herein can be extended as a general/universal attaching of NTA or other chelators onto proteins/peptides with high degree of efficiency.

Example 6

Detection of Polyhistidine-Containing Proteins on a Nitrocellulose Membrane

SDS PAGE and Western Blotting

Figure 6:
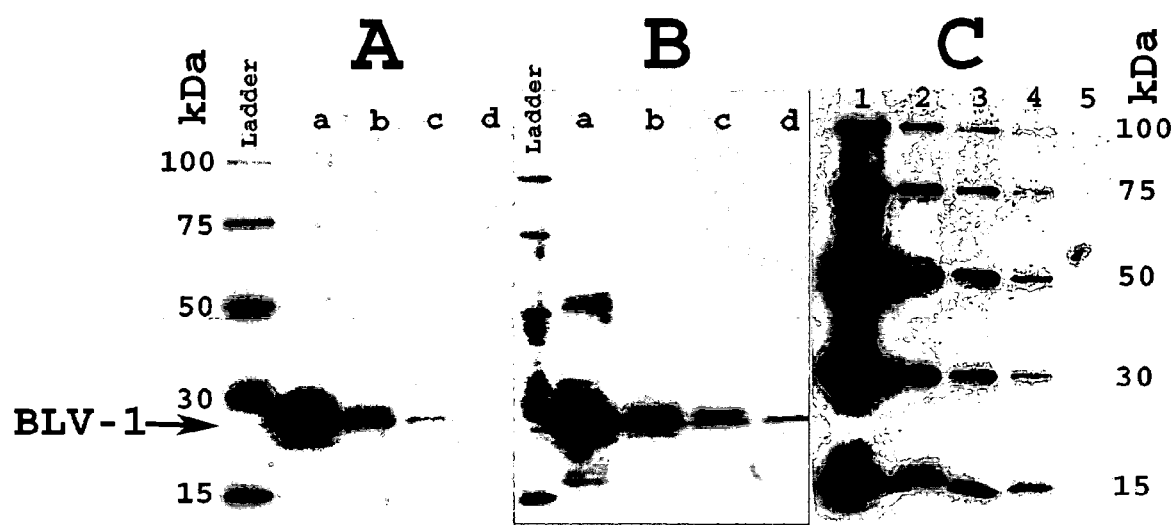
FIG. 6 shows the detection of His-tagged proteins with HRP-Ni (panels A and B) or HRP-Zn (panel C) conjugate.

FIG. 6 shows the detection of His-tagged proteins with HRP-Ni (panels A and B) or HRP-Zn (panel C) conjugate of this invention. FIG. 6A shows the detection of BLV-1 using HRP chemiluminescent substrate, where lanes a, b, c and d represent 1 µg, 200 ng, 40 ng and 8 ng, respectively. The ladder lane denotes a standard His-tag protein ladder, with the respective kDa. FIG. 6B shows the detection of BLV-1 using HRP chromogenic substrate, where lanes a, b, c and d represent x, x, x and x, respectively. The ladder lane denotes a standard His-tag protein ladder, with the respective kDa. FIG. 6C shows the detection of the 5 polyhistidine containing molecular weight marker proteins using HRP chemiluminescent substrate, where lanes 1, 2, 3, 4, and 5 represent 50 ng, 12.5 ng, 3.1 ng, 0.8 ng and 0.2 ng, respectively. For chemiluminescent detection the HRP-Ni (panel A) and HRP-Zn (panel C) conjugates were maintained at 20 ng and 50 ng in 20 mL, respectively. For the chromogenic detection presented in panel B, the HRP-Ni was maintained at 2 µg in 20 mL.

Description of the Assay.

The proteins were fractionated over SDS-PAGE gel and were transferred onto nitrocellulose membrane using standard western blotting protocol. Blocking membrane, incubating with conjugate, and detecting with the substrate is as described above.

Results and Conclusion

Each of the five His-tagged molecular weight marker and the BLV-1 bands were efficiently detected implying the strong interaction between the HRP-Ni or HRP-Zn of this invention and the polyhistidine motif.

REFERENCES

Metal chelate affinity chromatography, a new approach to protein fractionation. Porath J et al., Nature 258 (1975), 598-9.

Interaction of hexahistidine fusion proteins with Nitrilotriacetic Acid-Chelated Ni2+ Ions. Methods: A companion to Methods in enzymology 4 (1992), 68-72.

Nakane, P. K, and Kawaoi, A. Peroxidase-labeled Antibody. A new method of conjugation. *J. Histochem. Cytochem* 22 (1974), 1084-1091.

Expression of a bispecific dsFv-dsFv' antibody fragment in *Escherichia coli*. Schmiedl A. et al., Protein Engineering 13 (2000), 725-734.

Hydrazine-based and carbonyl-based bifunctional crosslinking reagents—U.S. Patent No. 20030013857 (Schwartz, David A.) Solulink Incorporated.

Immunoassay technique using Histidine tags, metals, and chelating Agents—U.S. Pat. No. 5,674,677 (Peterson, Darell L.) The Center for Innovative Technology, Herdon, Va.

Metal chelate resins—U.S. Pat. No. 5,047,513 (Dobeli, Heinz and Hochuli, Frich) Hoffman-La Roche Inc.

Technique for joining amino acid sequences and novel composition useful in immunoassays—U.S. Pat. No. 5,840,834 (Peterson, Darell L.) Virginia Commonwealth University.

What is claimed is:

1. A compound having the formula:

[Chel]-[linker]-X—CO—Ar-D wherein,

[Chel] is a metal chelating moiety selected from the group consisting of nitrilotriacetic acid (NTA), iminodiacetic acid (IDA), bicinchoninic acid (BCA) and N,N,N'-tris (carboxymethyl)ethylenediamine (TED);

[linker] is a substituted or unsubstituted $(C_{1-8})$alkyl;

X is NR, —NR—NR—, or S,

Ar is substituted or unsubstituted $(C_{6-10})$aryl or $(C_{5-10})$ heteroaryl; and D is selected from the group consisting of —CHO, —NRNR$^1$R$^2$, and —Nh—N=CR$^1$R$^2$, wherein R, R$^1$ and R$^2$ are independently selected from hydrogen or substituted or unsubstituted $(C_{1-4})$alkyl.

2. The compound according to claim 1 wherein Ar is a substituted or unsubstituted phenyl or pyridine ring.

3. The compound according to claim 1 wherein D is selected from —CHO, —NHNH$_2$ and —NH—N=CR$^1$R$^2$, wherein R$^1$ and R$^2$ are $(C_{1-4})$ alkyl.

4. The compound of claim 2 having a formula A, B or C:

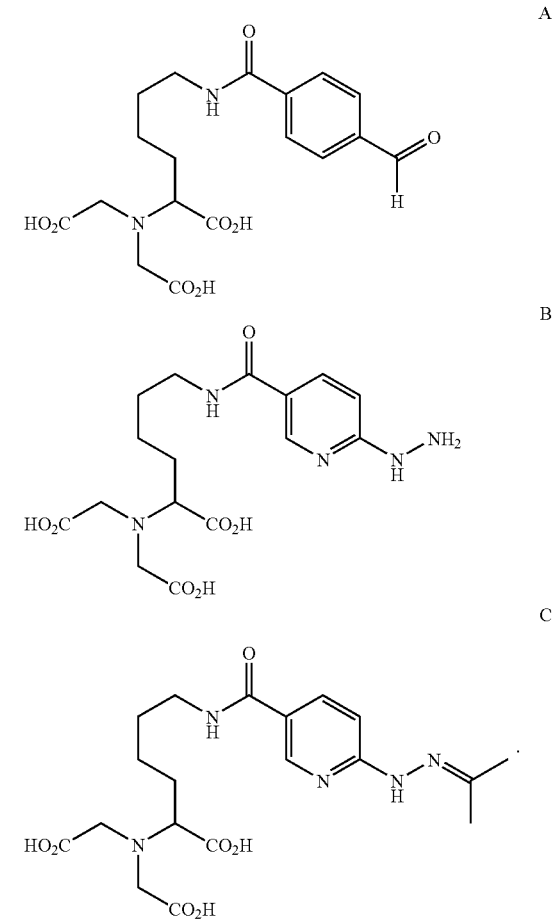

* * * * *